United States Patent
Ruiz Canovas et al.

(10) Patent No.: US 11,071,707 B2
(45) Date of Patent: Jul. 27, 2021

(54) COMPOSITIONS FOR PROTECTING SKIN COMPRISING DNA REPAIR ENZYMES AND PHYCOBILIPROTEIN

(71) Applicant: GREENALTECH, S.L., Barcelona (ES)

(72) Inventors: Eugenia Ruiz Canovas, Barcelona (ES); María Teresa López Cerro, Portocolom-Felanitx (ES); Derek Georges Latil de Ros, Girona (ES); Olga Durany Turk, Barcelona (ES); Jordi Segura de Yebra, Barcelona (ES); Jaume Mercadé Roca, Barcelona (ES)

(73) Assignee: ALGAKTIV, S.L., Barcelona (ES)

( * ) Notice: Subject to any disclaimer, the term of this patent is extended or adjusted under 35 U.S.C. 154(b) by 82 days.

(21) Appl. No.: 15/746,287

(22) PCT Filed: Jul. 20, 2016

(86) PCT No.: PCT/EP2016/067328
§ 371 (c)(1),
(2) Date: Jan. 19, 2018

(87) PCT Pub. No.: WO2017/013183
PCT Pub. Date: Jan. 26, 2017

(65) Prior Publication Data
US 2018/0207079 A1 Jul. 26, 2018

(30) Foreign Application Priority Data
Jul. 21, 2015 (EP) ..................................... 15382376

(51) Int. Cl.
| | |
|---|---|
| *A61K 8/66* | (2006.01) |
| *A61K 38/16* | (2006.01) |
| *A61K 38/51* | (2006.01) |
| *A61Q 17/04* | (2006.01) |
| *A61Q 19/08* | (2006.01) |
| *A61K 35/748* | (2015.01) |

(52) U.S. Cl.
CPC .............. *A61K 8/66* (2013.01); *A61K 35/748* (2013.01); *A61K 38/164* (2013.01); *A61K 38/51* (2013.01); *A61Q 17/04* (2013.01); *A61Q 19/08* (2013.01); *C12Y 401/99003* (2013.01)

(58) Field of Classification Search
CPC .......... A61K 8/66; A61K 38/15; A61K 38/51; A61K 35/748; A61Q 17/04; A61Q 19/08; C12Y 401/99003
See application file for complete search history.

(56) References Cited

U.S. PATENT DOCUMENTS 8,383,167 B2 * 2/2013 Corstjens ............... A61Q 19/02
424/725
2006/0257509 A1 11/2006 Zimmerman et al.

OTHER PUBLICATIONS

Delsin et al. Clinical Efficacy of Dermocosmetic Formulations Containing Spirulina Extract on Young and Mature Skin: Effects on teh Skin Hydrolipidic Barrier and Structural Properties; Clinical Pharmacology and Biopharmaceutics, vol. 4, No. 4, pp. 1-5. (Year: 2015).*
Stege et al. Enzyme Plus Light Therapy to Repair DNA Damage in Ultraviolet-B-Irradiated Human Skin; PNAS, vol. 97, No. 4, pp. 1790-1795. (Year: 2000).*
Manconia et al. Phycocyanin Liposomes for Topical Anti-Inflammatory Activity: In Vitro In Vivo Studoes; Journal of Pharmacy and Pharmacology, vol. 61, pp. 423-430. (Year: 2009).*
Gupta et al. Isolation of C-Phycocyanin From *Synechococcus* Sp., (Anacystis Nidulans BD1); Journal of Applied Phycology, vol. 22, pp. 231-233. (Year: 2010).*
Golecki et al. Studies on Ultrastructure and Composition of Cell Walls of the Cyanobacterium Anacystis Nidulans; Archives of Micobiology, vol. 114, pp. 35-41. (Year: 1977).*
Padula et al. Photodynamic Action of Phycocyanin: Damage and Repair; Journal of Photochemistry and Photobiology B: Biology, 32, pp. 19-26. (Year: 1996).*
Pazzaglia et al., "Activation of Metalloproteinases-2 and -9 by Interleukin-1a- in S100A4-positive Liposarcoma Cell Line: Correlation with Cell Invasiveness", 2004, Anticancer Res., vol. 24, pp. 967-972.
"Anti-Ageing Sun Care for Face SPF30", Laboratories Thalion, database accession No. 2537189, from Mintel's Global New Products Database (GNPD), 4 pgs.
"Performance Booster", Laboratoire Mergens, database accession No. 1112796, from Mintel's Global New Products Database (GNPD), 2 pgs.
"Spirulina", Frenchtop Natural, database accession No. 1507355, from Mintel's Global New Products Database (GNPD), 4 pgs.
GenoFix® CPD, retrieved from the Internet on Nov. 18, 2015 from URL: <http://www.carlosessa.it/en/news>, 4 pgs.

* cited by examiner

*Primary Examiner* — Susan M Hanley
*Assistant Examiner* — Paul C Martin
(74) *Attorney, Agent, or Firm* — Melvin Li; Heslin Rothenberg Farley & Mesiti PC

(57) ABSTRACT

The present invention is concerned with a composition for repairing human skin. Specifically, the composition has a DNA repair enzyme and at least one phycobiliprotein. The DNA repair enzyme is a photolyase, and the photolyase and/or the phycobiliprotein is encapsulated by liposomes. The composition is effective in repairing damage to human skin as a result of environment daily stress, sun exposure, or premature-aging.

10 Claims, No Drawings

COMPOSITIONS FOR PROTECTING SKIN COMPRISING DNA REPAIR ENZYMES AND PHYCOBILIPROTEIN

CROSS REFERENCE TO RELATED APPLICATIONS

This application is a national stage filing under section 371 of International Application No. PCT/EP2016/067328, filed on Jul. 20, 2016, published in English on Jan. 26, 2017, as WO2017/013183 A1 and which claims priority to European Application No. 15382376.0, filed on Jul. 21, 2015, the entire disclosure of these applications being hereby incorporated herein by reference.

FIELD OF THE INVENTION

The invention relates to a composition comprising a DNA repair enzyme and at least one phycobiliprotein, as well as to the use of said composition in the therapeutic and cosmetic treatment of the skin.

BACKGROUND OF THE INVENTION

Chronic excessive exposure to ultraviolet radiation (UVR) from sunlight is a causative factor in the development of photoaging and skin malignancies. UV radiation can damage DNA molecules in the skin cells by cross-linking adjacent pyrimidines on the same DNA strand and fanning pyrimidine dimmers. The harmful effects of UVR from sunlight are currently considered the major environmental risk factor for skin cancer and a complete carcinogen by damaging DNA and suppressing immune responses. Other environmental factors such as free oxygen radicals, harsh chemicals, sun exposure and daily stress have also adverse effects on human skin.

Cells have developed several cellular mechanisms for repairing and removing the DNA damage. However, when the DNA damages are incurred too fast, the DNA repair system becomes overloaded. Consequently, un-repair DNA damages start to accumulate and, if reaching certain threshold, may lead to pre-mature skin aging or even cancerous development in the skin.

In many organisms, the photolyase enzyme mediates DNA repair. In this regard, previous studies have shown that topical treatments utilizing photolyase may be effective in reducing the risk of skin cancer in patients with defective DNA repair.

The anti-aging compositions known from the prior art comprise other components which counteract light-induced aging in addition to photolyase such as retinoic acid and retinol as preferred components. Retinoids engage in the metabolism of the skin cells and, besides stimulating the proliferation and differentiation of the epidermal keratinocytes, increase the production of collagen by fibroblast. In addition, retinol is said to reduce the formation of collagen-digesting enzymes. However, retinoic acid has teratogenous properties and has a relatively high cell toxicity and, more particularly, phototoxicity and, accordingly, may only be used in low concentration in compositions intended for human application. In addition, retinol is readily degraded by oxidation under the effect of light and/or heat and is difficult to stabilize in cosmetic and pharmaceutical formulations.

Phycobiliproteins play an important role on many commercial applications such as colorant for food and cosmetic products. Furthermore, phycobiliproteins are widely used in industry and clinical or research immunology laboratories as fluorophores due to their physicochemical properties.

Therefore, there is a necessity in the state of the art to provide more suitable preparations that can effectively ameliorate the adverse effects on the skin, rejuvenate the skin and improve the appearance and conditions of the skin.

BRIEF DESCRIPTION OF THE INVENTION

The inventors of the present invention have discovered that, surprisingly, the combination of DNA repair enzymes with phycobiliproteins shows enhanced protective and restorative activity of skin cell against environmental aggression, mainly to oxidative stress and UVB radiation.

Thus, in a first aspect, the invention relates to a composition comprising a DNA repair enzyme and at least one phycobiliprotein.

In a second aspect, the invention relates to a pharmaceutical composition comprising the composition defined in the first aspect of the invention and a pharmaceutically acceptable vehicle.

In a third aspect, the invention relates to a cosmetic composition comprising the composition defined in the first aspect of the invention and a cosmetically acceptable vehicle.

In a fourth aspect, the invention relates to the composition defined in the first aspect of the invention for use in medicine.

In a fifth aspect, the invention relates to the composition defined in the first aspect of the invention for use in the treatment and/or the prevention of skin cancer, actinic keratosis, solar erythema and/or sunburn in a subject.

Finally, in a sixth aspect, the invention relates to a cosmetic method for preventing the premature-aging on skin which comprises administering to a subject the cosmetic composition defined in the third aspect of the invention.

DETAILED DESCRIPTION OF THE INVENTION

Compositions of the Invention

In a first aspect, the invention relates to a composition, hereinafter referred as "the composition of the invention", comprising a DNA repair enzyme and at least one phycobiliprotein.

The term "composition", as used herein, relates to a material composition that comprises at least two components, as well as any product resulting, directly or indirectly, from the combination of the different components in any quantity thereof. Those skilled in the art will observe that the composition may be formulated as a single formulation or may be presented as separate formulations of each of the components, which may be combined for joint use as a combined preparation. The composition may be a kit-of-parts wherein each of the components is individually formulated and packaged.

The term "DNA repair enzyme" as used herein, relates to an enzyme that is able to repair DNA. Such DNA repair enzymes are often categorized by the type of DNA damage they repair. Thus, said DNA repair enzyme may be a base excision repair (BER) enzyme if it repairs damage to a single nitrogenous base. Illustrative examples of BER enzymes include but are not limited to uracil-DNA glycosylase (UNG), single strand selective monofunctional uracil DNA glycosylase (SMUG1), 3,N(4)-ethenoeytosine glycosylase (MBD4), thymine DNA-glycosylase (TDG), A/G-specific adenine DNA glycosylase (MUTYH), 8-oxoguanine DNA glycosylase (OGG1), endonuclease III-like (NTHL1), 3-methyladenine DNA glycosidase (MPG), DNA glycosylase/AP lyase (NEIL1 or 2), AP endonuclease (APEX 1 and 2), DNA ligase (LIG-3), ligase accessory factor (XRCC1), DNA 5'-kinase/3'-phosphatase (PNKP), ADP-ribosyltransferase (PARP 1 or 2) and T4 endonuclease V (T4N5).

Said DNA repair enzyme may be a nucleotide excision repair (NER) enzyme if it repairs damaged DNA which commonly consists of bulky, helix-distorsioning damage such as pyrimidine dimerization caused by UV light. Illustrative examples of NER enzymes include but are not limited to xeroderma pigmentosum group C-complementing protein (XPC), RAD23, caltracin isoform (CETN2), RPA Protein 1, 2 or 3, 3' to 5' DNA helicase (ERCC3), 5' to 3' DNA helicase, basic transcription factor (GTF2H1, GTF2H2, GTF2H3, GTF2H4, GTF2H5), CDK activating kinase (CDK7, CCNH), cyclin G1-interacting protein (MNAT1), DNA excision repair protein ERCC-51, excision repair cross-complementing 1 (ERCC1), DNA ligase 1 (LIG1), ATP-dependent helicase (ERCC6), photolyase, and the like.

Said DNA repair enzyme may be a mismatch repair (MMR) enzyme if it corrects errors in DNA which are not corrected by proofreading. Illustrative examples of MMR enzymes include but are not limited to MutS protein homolog (MSH2), mismatch repair protein (MSH3), MutS homolog 4 (MS114), MutS homolog 5 (MSH5), or G/T mismatch-binding protein (MSH6), DNA mismatch repair protein (PMS1, PMS2, MLH1, MLH3), Postmeiotic segregation increased 2-like protein (PMS2L3), and postmeiotic segregation increased 2-like 4 pseudogene (PMS2L4).

In a particular and preferred embodiment of the invention, said DNA repair enzyme is a photolyase. The term "photolyase", as used herein, relates to a DNA repair enzyme that repairs damage caused by exposure to ultraviolet light (UV). This enzyme mechanism requires visible light, preferentially from the violet/blue end of the spectrum and is known as photoreactivation. Photolyases bind complementary DNA strands and break certain types of pyrimidine dimers that arise when a pair of thymine or cytosine bases on the same strand of DNA becomes covalently linked. These dimers result in a bulge of the DNA structure, referred to a lesion. Photolyases have a high affinity for these lesions and reversibly bind and convert them back to the original bases. Depending on the cofactor which is used during the DNA reparation, photolyases are classified into folato photolyases if they use flavin and folate as cofactors or deazaflavin photolyases if the use flavin and deazaflavin as cofactors. In a particular and preferred embodiment of the invention, said photolyase is a deazaflavin photolyase.

The photolyase of the composition of the invention can be obtained from nature, i.e., isolated from an organism producing said protein, or it can be produced by synthetic or recombinant techniques.

In a particular embodiment, said photolyase is naturally produced. In a more particular embodiment, said photolyase is selected from the group consisting of: *Anacystis nidulans* photolyase, *Dunaliella salina* photolyase, *Haematococcus pluvialis* photolyase, *Botryococcus* sp. photolyase, *Chlorella* sp. photolyase, *Porphydium* sp. photolyase, *Spirulina* sp. photolyase, *Hordeum* sp. photolyase, *Zea mays* photolyase, *Triticum* sp. photolyase, *Nicotiana* sp. photolyase and *Arabidopsis thaliana* photolyase. In a more particular and preferred embodiment of the invention, said photolyase is from *Anacystis nidulans*. The composition defined in the first aspect of the invention also comprises at least one phycobiliprotein. The term "phycobiliprotein", as used herein, refers to a family of soluble and stable fluorescent proteins derived from cyanobacteria and eukaryotic algae. These proteins contain covalently linked tetrapyrrole groups that play a biological role in collecting light and, through fluorescence resonance energy transfer, conveying it to a special pair of chlorophyll molecules located in the photosynthetic reaction centre. Phycobiliproteins are formed of a complex between proteins and covalently bound phycobilins that act as chromophores.

In a particular embodiment, said phycobiliprotein is selected from the group consisting of C-phycocianin, allophycocianin, B-phycoerithrin and mixtures thereof. In a more particular and preferred embodiment of the invention, said phycobiliprotein is C-phycocianin. In another preferred embodiment of the invention, said phycobiliprotein is allophycocianin. In another preferred embodiment of the invention, said phycobiliprotein is a mixture of C-phycocianin and allophycocianin.

The phycobiliprotein of the composition of the invention can be obtained from nature, i.e., isolated from an organism producing said protein, or it can be produced by synthetic or recombinant techniques.

In a particular embodiment, said phycobiliprotein is naturally produced. In a more particular embodiment, said phycobiliprotein is selected from the group consisting of: *Anacystis nidulans* phycobiliprotein, *Spirulina* sp. phycobiliprotein and *Porphyridium cruentum* phycobiliprotein. In a more particular and preferred embodiment of the invention, said phycobiliprotein is from *Anacystis nidulans*.

In a preferred embodiment of the invention, said DNA repair enzyme and said phycobiliprotein are naturally produced by *Anacystis nidulans*.

If the DNA repair enzyme and/or the phycobiliprotein of the composition is naturally produced, it can be isolated and, optionally, purified by any suitable technique known by the person skilled in the art. The purification of the DNA repair enzyme and/or the phycobiliprotein requires that the cells in which the protein is expressed (i.e. *Anacystis nidulans*) are lysed. The skilled person will understand that the purification can be carried out by applying a single lysis step so that all biological membranes are disrupted, including the cell membrane and the mitochondrial membranes, thereby obtaining a whole cell lysate which can then be further processed in order to purify the DNA repair enzyme and/or the phycobiliprotein. The step of lysing the cells can be achieved by any convenient means, including, but not limited to, heat-induced lysis, adding a base, adding an acid, using enzymes such as proteases and polysaccharide degradation enzymes such as amylases, using ultrasound, mechanical lysis (i.e., subjecting the biomass to pressure sufficient to lyse the cells, termed "pressing"), using osmotic shock, infection with a lytic virus, or expression of one or more lytic genes. Lysis is performed to release intracellular molecules which have been produced by the cell. Each of these methods for lysing cells can be used as a single method or in combination simultaneously or sequentially. The extent of cell disruption can be observed by microscopic analysis.

The lysate or extract can be isolated or extracted from a cell by adding a base to a suspension containing the cells. The base should be strong enough to hydrolyze at least a portion of the protein compounds of the cells. Bases which are useful for solubilizing proteins are known in the state of the art. Exemplary bases which are useful in the present invention include, but are not limited to, hydroxides, carbonates and bicarbonates of lithium, sodium, potassium, calcium, and mixtures thereof. The lysate or extract can be isolated or extracted from a cell by using an enzyme.

Suitable enzymes to be used according to the present invention include but are not limited to, proteases and polysaccharide-degrading enzymes such as hemicellulase, pectinase, cellulase, driselase, proteases, chymotrypsin, and proteinase K. Any combination of a protease and a polysaccharide-degrading enzyme can also be used. The lysate or extract can be isolated or extracted from a cell using an expeller press. In this process, cells are forced through a screw-type device at high pressure, lysing the cells and causing the intracellular product to be released and separated from the protein and fiber (and other components) in the cell. The lysate or extract can be isolated or extracted from a cell by using ultrasound, i.e., sonication. Thus, cells can also be lysed with high frequency sound. The sound can be produced electronically and transported through a metallic tip to an appropriately concentrated cellular suspension. This sonication (or ultrasonication) disrupts cellular integrity based on the creation of cavities in cell suspension. The lysate or extract can be isolated or extracted from a cell by mechanical lysis. Cells can be lysed mechanically and optionally homogenized to facilitate collection of the product. For example, a pressure disrupter can be used to pump a cell containing slurry through a restricted orifice valve. High pressure is applied, followed by an instant expansion through an exiting nozzle. Typically, cell disruption is accomplished by three different mechanisms: impingement on the valve, high liquid shear in the orifice, and sudden pressure drop upon discharge, causing an explosion of the cell. The method releases intracellular molecules. Alternatively, a ball mill can be used. In a ball mill, cells are agitated in suspension with small abrasive particles, such as beads. Cells break because of shear forces, grinding between beads, and collisions with beads. The beads disrupt the cells to release cellular contents. Cells can also be disrupted by shear forces, such as with the use of blending (such as with a high speed or Waring® blender), the french press, or even centrifugation in case of weak cell walls, to disrupt cells. The lysate or extract can be isolated or extracted from a cell by applying an osmotic shock. The lysate or extract can be isolated or extracted from a cell by infecting the cells with a lytic virus. A wide variety of viruses to lyse cells suitable for use in the present invention, are well known by the person skilled in the art.

In a particular embodiment, the composition of the invention comprises a DNA repair enzyme and at least one phycobiliprotein with the proviso that no additional components are present in said composition.

In a more particular embodiment, the percentage by weight of the DNA repair enzyme in the composition of the invention is from about 0.00001% to 99.99999% and/or the percentage by weight of phycobiliprotein in the composition of the invention is from about 99.99999% to 0.00001%.

In another more particular embodiment, the percentage by weight of the DNA repair enzyme in the composition of the invention is from about 0.0001% to 99.9999% and/or the percentage by weight of phycobiliprotein in the composition of the invention is from about 99.9999% to 0.0001%.

In another more particular embodiment, the percentage by weight of the DNA repair enzyme in the composition of the invention is from about 0.001% to 99.999% and/or the percentage by weight of phycobiliprotein in the composition of the invention is from about 99.999% to 0.001%.

In another more particular embodiment, the percentage by weight of the DNA repair enzyme in the composition of the invention is from about 0.01% to 99.99% and/or the percentage by weight of phycobiliprotein in the composition of the invention is from about 99.99% to 0.01%.

In another more particular embodiment, the percentage by weight of the DNA repair enzyme in the composition of the invention is from about 0.1% to 99.9% and/or the percentage by weight of phycobiliprotein in the composition of the invention is from about 99.9% to 0.1%.

In another more particular embodiment, the percentage by weight of the DNA repair enzyme in the composition of the invention is from about 1% to 99% and/or the percentage by weight of phycobiliprotein in the composition of the invention is from about 99% to 1%.

In another particular embodiment, the percentage by weight of the DNA repair enzyme in the composition of the invention is 10% and the percentage by weight of phycobiliprotein in the composition of the invention is 90%. In another particular embodiment, the percentage by weight of the DNA repair enzyme in the composition of the invention is 20% and the percentage by weight of phycobiliprotein in the composition of the invention is 80%. In another particular embodiment, the percentage by weight of the DNA repair enzyme in the composition of the invention is 30% and the percentage by weight of phycobiliprotein in the composition of the invention is 70%. In another particular embodiment, the percentage by weight of the DNA repair enzyme in the composition of the invention is 40% and the percentage by weight of phycobiliprotein in the composition of the invention is 60%. In another particular embodiment, the percentage by weight of the DNA repair enzyme in the composition of the invention is 50% and the percentage by weight of phycobiliprotein in the composition of the invention is 50%. In another particular embodiment, the percentage by weight of the DNA repair enzyme in the composition of the invention is 60% and the percentage by weight of phycobiliprotein in the composition of the invention is 40%. In another particular embodiment, the percentage by weight of the DNA repair enzyme in the composition of the invention is 70% and the percentage by weight of phycobiliprotein in the composition of the invention is 30%. In another particular embodiment, the percentage by weight of the DNA repair enzyme in the composition of the invention is 80% and the percentage by weight of phycobiliprotein in the composition of the invention is 20%. In another particular embodiment, the percentage by weight of the DNA repair enzyme in the composition of the invention is 90% and the percentage by weight of phycobiliprotein in the composition of the invention is 10%.

As the person skilled in the art knows, the composition of the invention includes an appropriate concentration of the DNA repair enzyme and an appropriate concentration of the phycobiliprotein; thus, an appropriate ratio between DNA repair enzyme/phycobiliprotein. The ratio may be expressed in terms of molarity, i.e. molar ratio. The term "molar ratio" as used herein refers to the ratio between the amount in moles of any two compounds (i.e. DNA repair enzyme and phycobiliprotein) involved a reaction or interaction. In a particular embodiment, said molar ratio between DNA repair enzyme/phycobiliprotein is at least from about 1:20 to about 20:1, at least from about 1:15 to about 15:1, at least from about 1:10 to about 10:1, at least from about 1:9 to about 9:1, at least from about 1:8 to about 8:1, at least from about 1:7 to about 7:1, at least from about 1:6 to about 6:1, at least from about 1:5 to about 5:1, at least from about 1:4 to about 4:1, at least from about 1:3 to about 3:1, at least from about 1:2 to about 2:1 or at least 1:1. In a preferred embodiment, said molar ratio is 1:6. In another preferred embodiment, said molar ratio is 1:10.

As mentioned above, in a particular embodiment, the phycobiliprotein of the composition of the invention is a mixture of C-phycocianin and allophycocianin. In this event, in a still more preferred embodiment, the phycobiliprotein of the composition of the invention includes an appropriate concentration of C-phycocianin and an appropriate concentration of allophycocinain; thus, an appropriate ratio between C-phycocianin/allophycocianin. In a particular embodiment, said molar ratio between C-phycocianin/allophycocianin is at least from about 1:20 to about 20:1, at least from about 1:15 to about 15:1, at least from about 1:10 to about 10:1, at least from about 1:9 to about 9:1, at least from about 1:8 to about 8:1, at least from about 1:7 to about 7:1, at least from about 1:6 to about 6:1, at least from about 1:5 to about 5:1, at least from about 1:4 to about 4:1, at least from about 1:3 to about 3:1, at least from about 1:2 to about 2:1 or at least 1:1. In a preferred embodiment, said molar ratio is 1:10.

In another particular embodiment, the composition of the invention comprises a DNA repair enzyme, at least one phycobiliprotein and at least one additional component which will be described below. In this particular embodiment, the person skilled in the art knows that the sum of the percentages of the components of the composition of the invention does not exceed 100% by weight. In a more particular embodiment, the percentage by weight of the DNA repair enzyme and/or the percentage by weight of phycobiliprotein in the composition of the invention is from about 0.001% to about 0.01%. In another more particular embodiment, the percentage by weight of the DNA repair enzyme and/or the percentage by weight of phycobiliprotein in the composition of the invention is from about 0.01% to about 0.1%. In another more particular embodiment, the percentage by weight of the DNA repair enzyme and/or the percentage by weight of phycobiliprotein in the composition of the invention is from about 0.1% to about 1%. In another more particular embodiment, the percentage by weight of the DNA repair enzyme and/or the percentage by weight of phycobiliprotein in the composition of the invention is from about 1% to about 5%. In another more particular embodiment, the percentage by weight of the DNA repair enzyme and/or the percentage by weight of phycobiliprotein in the composition of the invention is from about 5% to about 10%. In another more particular embodiment, the percentage by weight of the DNA repair enzyme and/or the percentage by weight of phycobiliprotein in the composition of the invention is from about 10% to about 20%. In another more particular embodiment, the percentage by weight of the DNA repair enzyme and/or the percentage by weight of phycobiliprotein in the composition of the invention is from about 5% to about 10%. In another more particular embodiment, the percentage by weight of the DNA repair enzyme and/or the percentage by weight of phycobiliprotein in the composition of the invention is from about 10% to about 20%. In another more particular embodiment, the percentage by weight of the DNA repair enzyme and/or the percentage by weight of phycobiliprotein in the composition of the invention is from about 20% to about 30%. In another more particular embodiment, the percentage by weight of the DNA repair enzyme and/or the percentage by weight of phycobiliprotein in the composition of the invention is from about 30% to about 40%. In another more particular embodiment, the percentage by weight of the DNA repair enzyme and/or the percentage by weight of phycobiliprotein in the composition of the invention is from about 40% to about 50%.

In a preferred embodiment, the percentage by weight of the DNA repair enzyme in the composition of the invention is about 0.001%. In a preferred embodiment, the percentage by weight of the DNA repair enzyme in the composition of the invention is about 0.01%. In a more preferred embodiment, the percentage by weight of the DNA repair enzyme in the composition of the invention is about 0.02%, about 0.03%, about 0.04%, about 0.05%, about 0.06%, about 0.07%, about 0.08%, about 0.09%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 15%, about 20%, about 25%, about 30%, about 35%, about 40% about 45%, about 50%, about 55%, about 60%, about 65%, about 70%, about 75%, about 80%, about 85%, about 90%, about 95%, about 99% or more.

In another preferred embodiment, the percentage by weight of the phycobiliprotein in the composition of the invention is about 0.01%. In another preferred embodiment, the percentage by weight of the phycobiliprotein in the composition of the invention is about 0.02%, about 0.03%, about 0.04%, about 0.05%, about 0.06%, about 0.07%, about 0.08%, about 0.09%, about 0.1%, about 0.5%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 15%, about 20%, about 25%, about 30%, about 35%, about 40% about 45%, about 50%, about 55%, about 60%, about 65%, about 70%, about 75%, about 80%, about 85%, about 90%, about 95%, about 99% or more.

In a more preferred embodiment of the invention, the percentage by weight of the DNA repair enzyme is from about 0.001% to 0.01% and the percentage by weight of the phycobiliprotein is from about 0.01% to 0.1% in the composition of the invention.

In a particular embodiment of the invention, the DNA enzyme repair, preferably photolyase, is encapsulated by lipid vesicles either alone or in combination with the phycobiliprotein, preferably C-phycocianin. The liposomes may be made from natural and synthetic phospholipids, glycolipids, and other lipids and lipid congeners; cholesterol, cholesterol derivatives and other cholesterol congeners; charged species which impart a net charge to the membrane; reactive species which can react after liposome formation to link additional molecules to the liposome membrane; and other lipid soluble compounds which have chemical or biological activity. Liposomes facilitate the transfer of the composition of the invention into the dermis of the skin. The encapsulation of the components of the composition of the invention into liposomes can be done by any suitable method known in the art. Liposomes may be of various sizes and may have either one or several membrane layers separating the internal and external compartments. The most important elements in liposome structure are that a sufficient amount of enzyme be sequestered so that only one or a few liposomes are required to enter each cell for delivery of the DNA repair enzyme, and that the liposome be resistant to disruption. Liposome structures include small unilamellar vesicles (SUVs, less than 250 angstroms in diameter), large unilamellar vesicles (LUVs, greater than 500 angstroms in diameter), and multilamellar vesicles (MLs). SUVs can be isolated from other liposomes and unincorporated enzyme by molecular sieve chromatography, which is precise but time consuming and dilutes the liposomes, or differential centrifugation, which is rapid but produces a wider range of liposome sizes. Liposome membranes undergo a phase transition from crystalline to liquid at a temperature (Tc) characteristic of the phospholipid composition. When the phospholipid is heated above Tc and then cooled, the membrane retains water in its amphiphilic lattice and has the characteristics of a gel. In order to achieve the liquid or gel state, the phospholipid composition must be such that the Tc is lower than the temperature which inactivates the entrapped enzyme. Cholesterol in the phospholipid mix effectively reduces the Tc by broadening the range at which phase transition occurs. In view of these requirements, a suitable mixture for preparing the liposomes according to the present invention comprises phosphotidyl choline (or a derivative thereof with a Tc of less than 42° C.), dicetyl phosphate (or a negatively charged species at neutrality), and cholesterol (or a cholesterol derivative) at a molar ratio of 7:2:1.

In a particular embodiment of the invention, the liposomes comprise from about 60% to about 99% phosphatidylcholine.

Typically, pH sensitive liposomes are used. Accordingly, liposomes which are stable at neutral pH but release their contents at acidic pH can be used to deliver the composition of the invention into the lysozymes of the cytoplasm, whereupon the contents are released. Since DNA repair enzymes, like photolyase, and phycobiliproteins, like C-phycocianin, are relatively stable at low pH, this method allows efficient delivery of active enzymes into cells.

Liposomes can be made sensitive to the low pH of the lysozymes by the lipid composition. In particular, pH sensitive liposomes can be prepared by using phospholipids which form lipid bilayers when charged but fail to stack in an ordered fashion when neutralized. An example of such a phospholipid is phosphatidylethanolamine, which is negatively charged above pH 9. The net charge of a phospholipid can be maintained at a pH which would otherwise neutralize the head groups by including charged molecules in the lipid bilayer which themselves can become neutralized. Examples of these charged molecules are oleic acid and cholesteryl hemisuccinate, which are negatively charged at neutral pH but become neutralized at pH 5. The effect of combining these together in a lipid bilayer is that at pH 9 all molecules are charged; at pH 7 the net negative charge of the oleic acid and cholesteryl hemisuccinate maintains the stability of the phosphatidylethanolamine, and at pH 5 all components are protonated and the lipid membrane is destabilized. Additional neutral molecules, such as phosphatidylcholine, can be added to the liposomes as long as they do not interfere with stabilization of the pH sensitive phospholipid by the charged molecules.

If desired, the composition of the invention can be presented in the form of a formulation selected from the group consisting of creams, multiple emulsions, anhydrous compositions, aqueous dispersions, oils, milks, balms, foams, lotions, gels, cream gels, hydroalcoholic solutions, hydroglycolic solutions, hydrogels, liniments, sera, soaps, shampoos, conditioners, serums, salves, mousses, ointments, powders, sticks, pencils, sprays, aerosols, capsules, gelatin capsules, soft capsules, hard capsules, tablets, sugar-coated tablets, granulated forms, chewing gums, solutions, suspensions, emulsions, syrups, polysaccharide films, jellies and gelatin.

As mentioned above, the composition of the invention may contain one or more additional ingredients for further improving the efficacy of combination of the DNA repair enzyme and the phycobiliprotein in repairing the adverse effects of the environment, daily stress, sun exposure, or pre-mature aging on human skin, or in order to improving the aesthetics and stability of the compositions containing the DNA repair enzyme and the phycobiliprotein and so that such compositions are commercially acceptable. Such additional ingredients may include, but are not limited to: DNA repair enzymes, oils, surfactants, humectants, botanical extracts, vitamins, antioxidants, sunscreen agents, preservatives, and the like. The composition may be in the form of an emulsion, gel, suspension, aqueous solution, or in the anhydrous form. If present in the form of an emulsion, the composition may be in the form of a water-in-oil or oil-in-water emulsion. By way of illustration, ranges of water may be from about 0.1 to 99%, preferably from about 1-85%, more preferably from about 5 to 80% by weight of the total composition, and ranges of oil from are, illustratively, about 1-85%, preferably from about 3-80%, more preferably from about 5-75% by weight of the total composition. If the composition is present in the anhydrous form, it may also contain one or more oils. By way of illustration, ranges of oil may be from about 1 to 95% by weight of the total composition.

Illustrative examples of suitable DNA repair enzymes which may be used in the composition of the invention have been detailed above. In a particular embodiment, the composition of the invention comptises a (first) DNA repair enzyme (i.e. photolyase), at least one phycobiliprotein (i.e. C-phycocianin) and, in addition, a (second) DNA repair enzyme. If present, such DNA repair enzymes may range from about 0.001% to about 10%, preferably from about 0.001% to about 0.01%.

Suitable oils include materials also known as skin conditioning agents such as nonvolatile silicones, esters, paraffinic hydrocarbons, vegetable oils, and synthetic oils. The term "nonvolatile" as used herein means that the compound has a vapor pressure of less than about 2 mm of mercury at 20° C. Typically, the skin conditioning agent is characterized by a viscosity from about 5 to 10 centistokes at 25° C. up to about 1,000,000 centipoise at 25° C. Particularly preferred are the nonvolatile silicones, including but not limited to: amine functional silicones such as amodimethicone, phenyl substituted silicones such as bisphenylhexamethicone, trimethylsiloxyphenyl dimethicone, phenyl trimethicone, polyphenylmethylsiloxane, dimethicone, phenyl dimethicone, diphenyl dimethicone, and dimethicone substituted with $C_{2-30}$ alkyl groups such as cetyl dimethicone. Suitable esters include mono-, di-, or triesters. Monoesters are in the general form RCO—R' wherein R and R' are each independently a $C_{1-45}$ straight or branched chain, saturated or unsaturated alkyl. Diesters may be formed by the reaction of a $C_{1-45}$ aliphatic or aromatic mono- or dihydric alcohol with a $C_{1-45}$ aliphatic or aromatic mono- or dicarboxylic acid, as appropriate, where the aliphatic group may be straight or branched chain, or saturated or unsaturated. Suitable triesters include the reaction products of a $C_{1-45}$ aliphatic or aromatic alcohol having at least three hydroxyl groups with a $C_{1-45}$ carboxylic acid, or a $C_{1-45}$ aliphatic or aromatic alcohols with a $C_{1-45}$ tricarboxylic acid, with the aliphatic chains being linear or branched, saturated or unsaturated. Examples include esters of caprylic and capric acids and glycerin such as caprylic/capric triglycerides; esters of glycerin or polyglycerin and stearic acid such as glyceryl stearate, diglyceryl diisostearate; esters of malic acid and isostaryl alcohol such as diisostearyl malate; coca caprylate caprate and the like.

Humectants which may be used in the composition of the invention include glycols, sugars, and the like. Suitable glycols are in monomeric or polymeric form and include polyethylene and polypropylene glycols such as PEG 4-200, which are polyethylene glycols having from 4 to 200 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on. Preferably, the humectants used in the composition of the invention are $C_{1-6}$, preferably $C_{2-4}$ alkylene glycols, most particularly butylene glycol. If present, such humectants may range from about 0.001% to about 25%, preferably from about 0.005% to about 20%, more preferably from about 0.1% to about 15%, by total weight of the composition of the invention.

Suitable botanical extracts that may be used in the composition of the invention include extracts from plants (herbs, roots, flowers, fruits, seeds) such as flowers, fruits, vegetables, and so on, including yeast ferment extract, padica pavonica extract, thermus thermophilis ferment extract, camelina sativa seed oil, boswellia serrata extract, olive extract, aribodopsis thaliana extract, acacia dealbata extract, acer saccharinum (sugar maple), acidopholus, acorns, *aesculus, agaricus*, agave, agrimonia, algae, aloe, citrus, *brassica*, cinnamon, orange, apple, blueberry, cranberry, peach, pear, lemon, lime, pea, seaweed, caffeine, green tea, chamomile, willowbark, mulberry and poppy. Further specific examples include, but are not limited to, *Glycyrrhiza Glabra, Salix Nigra, Macrocycstis Pyrifera, Pyrus Malus, Saxifraga Sarmemosa, Vilis Vinifera, Moms Nigra, Scutellaria Baicalensis, Anthemis Nobilis, Salvia Sclarea, Rosmarinus Officianalis, Citrus Medica Limonum, Panax Ginseng*, and mixtures thereof. If presented, the amount of botanical extracts may range from about 0.0001% to about 10%, preferably from about 0.0005% to about 8%, more preferably from about 0.001% to about 5%, by total weight of the composition of the invention.

Humectants which may be used in the composition of the invention and include glycols, sugars, and the like. Suitable glycols are in monomeric or polymeric form and include polyethylene and polypropylene glycols such as PEG 4-200, which are polyethylene glycols having from 4 to 200 repeating ethylene oxide units; as well as $C1_6$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on. Preferably, the humectants used in the composition of the invention are $C1_6$, preferably $C2_4$ alkylene glycols, most particularly butylene glycol. If present, such humectants may range from about 0.001% to about 25%, preferably from about 0.005% to about 20%, more preferably from about 0.1% to about 15%, by total weight of the composition of the invention.

Sunscreen agents that can be used in the composition of the present invention include, but are not limited to: benzophenones and derivatives thereof (e.g., benzophenone 3, dioxybenzone, sulisobenzone, octabenzone, hydroxy- and/or methoxy-substituted benzophenones, and benzophenone sulfonic acids and salts thereof); salicylic acid derivatives (e.g., ethylene glycol salicylate, triethanolamine salicylate, octyl salicylate, homomenthyl salicylate, and phenyl salicylate); urocanic acid and derivatives thereof (e.g., ethyl urocanate); p-aminobenzoic acid (PABA) and derivatives thereof (e.g., ethyl/isobutyl/glyceryl esters thereof and 2-ethylhexyl p-dimethylaminobenzoate, which is also referred to as octyldimethyl PABA); anthranilates and derivatives thereof (e. g., o-amino-benzoates and various esters of amino-benzoic acid); benzalmalonate derivatives; benzimidazole derivatives; imidazolines; bis-benzazolyl derivatives; dibenzoylmethanes and derivatives thereof (e.g., 4-tert-butyl-4'-meth oxydibenzoylmethane, which is commonly referred to as "avobenzone," and 4-isopropyl-dibenzoylmethane); benzoxazole, benzodiazole, benzotriazoles, and derivatives thereof (e.g., 2-(2-hydroxy-5-methylphenyl)benzotriazole and methylene bis-benzotriazolyltetramethylbutylphenol, which is commonly referred to as "Tinosorb M"); diphenylacrylates and derivatives thereof (e.g., 2-ethylhexyl-2-cyano-3,3 diphenylacrylate, which is commonly referred to as "octocrylene," and ethyl-2-cyano-3,3-diphenylacrylate, which is commonly referred to as "etocrylene"); diesters or polyesters containing diphenylmethylene or 9H-fluorene substitutional groups; 2-phenyl-benzimidazole-5-sulphonic acid (PBSA); 4,4-diarylbutadienes; cinnamates and derivatives thereof (e.g., 2-ethylhexyl-p-methoxycinnamate, octyl-p-methoxy cinnamate, umbelliferone, methylumbelliferone, methylacetoumbelliferone, esculetin, methylesculetin, and daphnetin); camphors and derivatives thereof (e.g., 3-benzylidenecamphor, 4-methylbenzylidenecamphor, poly acrylamidomethyl benzylidenecamphor, benzylidene camphor sulfonic acid, and terephthalylidene dicamphor sulfonic acid); triazines and derivatives thereof (e.g., 2,4-bis-{[4-(2 ethyl-hexyloxy)-2-hydroxy]-phenyl}-6-(4-methoxyphenyl)-1,3,5-triazine, which is commonly referred to as "Tinosorb S"); naphthalates and derivatives thereof (e. g., diethylhexyl 2,6-naphthalate); naphtholsulfonates and derivatives thereof (e.g., sodium salts of 2-naphthol-3,6-disulfonic and 2-naphthol-6,8-disulfonic acids); dibenzalacetone and benzalacetonephenone; diphenylbutadienes and derivatives thereof; dihydroxynaphthoic acid and salts thereof; o- and p-hydroxybiphenyldisulfonates; coumarin derivatives (e. g., 7-hydroxy, 7-methyl, and 3-phenyl derivatives thereof); azoles/diazoles/triazoles and derivatives thereof (e.g., 2-acetyl-3-bromoindazole, phenyl benzoxazole, methylnaphthoxazole, and various aryl-benzotriazoles); quinine and derivatives thereof (e.g., bisulfate, sulfate, chloride, oleate, and tannate salts thereof); quinoline and derivatives thereof (e.g., 2-phenylquinoline and 8-hydroxyquinoline salts); tannic acid and derivatives thereof (e.g., hexaethylether derivatives thereof); hydroquinone and derivatives thereof; uric acid and derivatives thereof; vilouric acid and derivatives thereof, and mixtures or combinations thereof. Salts and otherwise neutralized forms of certain acidic sunscreens from the list hereinabove are also useful herein. Particularly preferred sunscreen agents for the present invention are: 4,4'-t-butyl methoxy-dibenzoylmethane, 2-ethylhexyl-2-cyano-3,3 diphenylacrylate, 2-ethylhexyl-salicylate, 3,3,5 trimethylcyclohexylsalicylate, 2-ethylhexyl p-methoxycinnamate, 2-hydroxy-4-methoxybenzophenone, 2,2-dihydroxy-4-methoxybenzophenone, 2,4-bis-{4-(2 ethyl-hexyloxy)-2-hydroxy]-phenyl}-6-(4-methoxyphenyl)-1,3,5-triazine, methylene bis-benzotriazolyl tetramethylbutylphenol, terephthalylidene dicamphor sulfonic acid, diethylhexyl 2,6-naphthalate, digalloyltrioleate, ethyl 4-[bis (hydroxypropyl)]aminobenzoate, glycerol p-aminobenzoate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl-sulfoniobenzoxazoic acid, and mixtures or combinations thereof. The above-described sunscreen agents may be used alone or in combination of two or more. In addition, other known animal or vegetable extracts having ultraviolet light absorbing ability may properly be used alone or in combination. If presented, the amount of sunscreen agents preferably ranges from about 0.001% to about 50%, preferably about 0.01% to about 10%, more preferably about 1% to about 5%, by total weight of the composition of the invention.

The composition of the present invention may further contain vitamins and/or antioxidants. Suitable vitamins may include ascorbic acid and derivatives thereof, such as ascrobyl palmitate; the B vitamins such as thiamine, riboflavin, pyridoxin, and the like; Vitamin A and the ester-based derivatives thereof, such as palmitate, acetate, and the like, as well as Vitamin A in the form of beta carotene; Vitamin E and derivatives thereof, such as Vitamin E acetate, nicotinate, or other esters thereof; Vitamins D and K; coenzymes such as thiamine pyrophoshate, flavin adenin dinucleotide (FAD), folic acid, pyridoxal phosphate, tetrahydrofolic acid, and the like. Suitable antioxidants include but are not limited to potassium sulfite, sodium bisulfite, sodium erythrobate, sodium metabisulfite, sodium sulfite, propyl gallate, cysteine hydrochloride, butylated hydroxytoluene, butylated hydroxyanisole, and so on. If presented, the amount of vitamins and/or antioxidants may each range from about 0.001% to about 10%, preferably from about 0.01% to about 8%, more preferably from about 0.05% to about 5%, by total weight of the composition of the invention.

The composition of the invention may also contain one or more surfactants, particularly if present in the emulsion form. Preferably such surfactants are nonionic and may be in the form of silicones or organic nonionic surfactants. Typically, suitable ranges are from about 0.1 to 40%, preferably from about 0.5 to 35%, more preferably from about 1 to 30% by weight of the total composition. Suitable silicone surfactants include but are not limited to polyorganosiloxane polymers that have amphiphilic properties, for example contain hydrophilic radicals and lipophilic radicals. These silicone surfactants may be liquids or solids at room temperature. Exemplary silicone surfactants that can be used in the present invention include, but are not limited to: dimethicone copolyols, alkyl dimethicone copolyols, and emulsifying silicone elastomers. Emulsifying silicone elastomers are elastomers that have one or more hydrophilic groups such as hydroxyl, oxyethylene, and the like bonded thereto so as to confer hydrophilic properties to the elastomer. Suitable organic nonionic surfactants may include alkoxylated alcohols or ethers formed by the reaction of an alcohol with a polyalkyleneoxide containing repeating units of alkylene oxide. Preferably, the alcohol is a fatty alcohol having 6 to 30 carbon atoms. Examples of organic nonionic surfactants that can be used in the present invention include, but are not limited to: steareth 2-100, beheneth 5-30, ceteareth 2-100, ceteth 1-45, and the like, which are formed by polyethyleneoxide with the corresponding stearyl/behenyl/cetyl alcohol (wherein the number as used herein designates the number of repeating units of ethylene oxide in the polyethyleneoxide). Other alkoxylated alcohols include esters formed by reaction of polymeric alkylene glycols with glyceryl fatty acid, such as PEG glyceryl oleates, PEG glyceryl stearate; or PEG polyhydroxyalkanotes such as PEG dipolyhydroxystearate wherein the number of repeating ethylene glycol units ranges from 3 to 1000. Moreover, suitable nonionic surfactants are formed by the reaction of a carboxylic acid with an alkylene oxide or with a polymeric ether. Monomeric, homopolymeric, or block copolymeric ethers, alkoxylated sorbitan, alkoxylated sorbitan derivatives can also be used as nonionic surfactants in the present invention.

The composition of the invention may also contain other ingredients such as structuring agents in the form of polymeric structuring agents such as acrylic polymers, polyamides or polyurethanes. The structuring agents may be water or oil soluble or dispersible. Such structuring agents will provide structure, or increase the viscosity of the composition. If present, suggested ranges are from about 0.1% to 50%, preferably from about 0.5% to 40%, more preferably from about 1% to 35% by weight of the total composition. Suitable structuring agents include natural, synthetic waxes, or mineral waxes such as petrolatum, candelilla, ozokerite, synthetic wax, polyethylene, and so on. Suitable polymeric structuring agents include acrylic polymers such as carbopol or pemulen (polymers of acrylic acid, methacrylic acid, or their simple esters crosslinked by polyfunctional agents such as allyl ethers of sucrose or pentaerythritol), ester or amide terminated polyamides such as those sold by Arizona Chemical under the UNICLEAR or SYLVACLEAR trademarks, or aqueous dispersions or solutions of polyurethanes.

In the case where the composition of the invention is colored particulates may be present. Illustratively, suggested ranges are from about 0.1% to 80%, more preferably from about 0.5% to 75%, more preferably from about 1 to 70% by weight of the total composition. The term "particulates" refers to pigments in the form of inorganic or organic pigments such as iron oxides (black, blue, red, yellow), or the D&C and FD&C Lakes. Particulates may also include ingredients commonly referred to as "powders" that is particulate materials that are present for muting color (such as titanium dioxide) or providing bulk to the composition. Further examples include nylon, polymethylmethacrylate, silica, silica silylate, and the like.

If desired, the composition of the invention may additionally comprise an adjuvant. Examples of adjuvants that can be used along with the composition of the invention include but are not limited to anti-inflammatory agents and/or analgesics, antipruritic agents, soothing agents, anesthetic agents, acetylcholine receptor aggregation inhibitors, muscle contraction inhibitors, anticholinergic agents, elastase inhibitors, matrix metalloprotease inhibitors, melanin synthesis stimulators or inhibitors, whitening or depigmenting, pro-pigmenting agents, self-tanning agents, anti-aging agents, NO-synthase inhibitors, 5α-reductase inhibitors, lysyl- and/or prolyl hydroxylase inhibitors, antioxidants, free radical scavengers and/or atmospheric anti-contamination agents, reactive carbonyl species scavengers, anti-glycation agents, antihistaminic agents, antiviral agents, antiparasitic agents, emulsifiers, emollients, organic solvents, liquid propellants, skin conditioners, moisture-retaining substances, alpha hydroxy acids, beta hydroxy acids, moisturizes, epidermal hydrolytic enzymes, vitamins, amino acids, proteins, dyes, biopolymers, gelling polymers, thickeners, surfactants, softening agents, emulsifying agents, binders, preservatives, anti-wrinkle agents, agents capable of reducing or treating bags under the eyes, exfoliating, agents antimicrobial agents, antifungal agents, fungistatic agents, bactericidal agents, bacteriostatic agents, dermal or epidermal macromolecule synthesis stimulators and/or agents capable of inhibiting or preventing degradation thereof, collagen synthesis stimulators, elastin synthesis stimulators, decorin synthesis stimulators, laminin synthesis stimulators, defensin synthesis stimulators, aquaporin synthesis stimulators, hyaluronic acid synthesis stimulators, fibronectin synthesis stimulators, sirtuin synthesis stimulators, heat shock protein synthesis stimulators, lipids and stratum corneum components synthesis stimulators, ceramides, fatty acids, collagen degradation inhibitors, elastin degradation inhibitors, serine protease inhibitors such as cathepsin G, fibroblast proliferation stimulators, keratinocyte proliferation stimulators, adipocyte proliferation stimulators, melanocyte proliferation stimulators, keratinocyte differentiation stimulators, adipocyte differentiation stimulators, acetylcholinesterase inhibitors, skin relaxing agents, glycosaminoglycan synthesis stimulators, antihyperkeratosis agents, comedolytic agents, antipsoriatic agents, DNA repair agents, DNA protecting agents, stabilizers, agents for treating and/or caring for sensitive skin, firming agents, anti-stretch mark agents, astringents, sebum production regulating agents, lipolytic agents or lipolysis stimulators, anti-cellulite agents, antiperspirants, healing stimulators, healing coadyuvants, re-epithelization stimulators, re-epithelization coadyuvants, cytokine growth factors, agents acting on capillary circulation and/or microcirculation, angiogenesis stimulators, vascular permeability inhibitors, venotonic agents, agents acting on cell metabolism, agents intended for improving dermis-epidermis junction, hair growth inducing agents, hair growth inhibitors or delaying agents, hair loss delaying agents, preservatives, perfumes, chelating agents, plant extracts, essential oils, marine extracts, agents from a biofermentation method, mineral salts, cell extracts, organic or mineral solar filters and photoprotective agents active against ultraviolet A and/or B rays and mixtures thereof.

Illustrative examples of anti-wrinkle agents and/or anti-aging agents include but are not limited to *Vitis vinifera* extract, *Rosa canina* extract, *Curcuma longa* extract, *Iris pallida* extract, *Theobroma cacao* extract, *Ginkgo biloba* extract, *Leontopodium alpinum* extract, *Dunaliella salina* extract, pentapeptide-18, acetyl hexapeptide-8, acetyl heptapeptide-4, acetyl octapeptide-3, acetyl tetrapeptide-5, tripeptide-10 citrulline, acetyl tripeptide-30 citrulline, diaminopropionoyl tripeptide-33, acetyl-tetrapeptide-22, dimethylmethoxy chromanol, dimethylmethoxy chromanyl palmitate, the mixture of hydrolyzed wheat protein, hydrolyzed soy protein and tripeptide-1, the mixture of *Pseudoalteromonas* ferment extract, hydrolyzed wheat protein, hydrolyzed soy protein, tripeptide-10 citrulline and tripeptide-1, *Pseudoalteromonas* ferment extract, the mixture of lysine.HCl, lecithin and tripeptide-10 citrulline, acetyl hexapeptide-30, acetylarginyltryptophyl diphenylglycine, acetyl tetrapeptide-22, other calcium channel antagonists, alverine, manganese or magnesium salts, magnesium gluconate, secondary or tertiary amines, retinol and its derivatives, idebenone and its derivatives, coenzyme Q10 and its derivatives, boswellic acid and its derivatives, GHK and its derivatives, carnosine and its derivatives.

Illustrative examples of anti-inflammatory and/or analgesic agents include but are not limited to madecasoside, echinacin, amaranth seed oil, sandalwood oil, peach leaf extract, extracts of *Aloe vera, Arnica montana, Artemisia vulgaris, Asarum maximum, Calendula officinalis, Capsicum, Centipeda cunninghamii, Chamomilla recutita, Crinum asiaticum, Hamamelis virginiana, Harpagophytum procumbens, Hypericum perforatum, Lilium candidum, Malva sylvestris, Melaleuca alternifolia, Origanum majorana, Origanum vulgare, Prunus laurocerasus, Rosmarinus officialis, Salix alba, Silybum marianum, Tanacetum parthenium, Thymus vulgaris, Uncaria guianensis* or *Vaccinum myrtillus*, mometasone furoate, prednisolone, non-steroidal anti-inflammatories, cyclooxygenase or lipoxygenase inhibitors, benzydamine, acetylsalicylic acid, rosmarinic acid, ursolic acid, derivatives of glycyrrhizinate, α-bisabolol, azulene and analogues, sericoside, ruscogenin, escin, scoline, rutin and analogues, hydrocortisone, clobetasol, dexamethasone, prednisone, paracetamol, amoxiprin, benorilate, choline salicylate, diflunisal, faislamine, methyl salicylate, magnesium salicylate, salsalate, diclofenac, aceclofenac, acemetacin, bromfenac, etodolac, indomethacin, oxametacin, proglumetacin, sulindac, tolmetin, ibuprofen, dexibuprofen, carprofen, fenbufen, fenoprofen, flurbiprofen, ketoprofen, dexketoprofen, ketorolac, loxoprofen, naproxen, miroprofen, oxaprozin, pranoprofen, tiaprofenic acid, suprofen, mefenamic acid, meclofenamate, meclofenamic acid, flufenamic acid, tolfenamic acid, nabumetone, phenylbutazone, azapropazone, clofezone, kebuzone, metamizole, mofebutazone, oxyphenbutazone, phenazone, sulfinpyrazone, piroxicam, lornoxicam, meloxicam, tenoxicam, celecoxib, etoricoxib, lumiracoxib, parecoxib, rofecoxib, valdecoxib, nimesulide, naproxcinod, fluproquazone or licofelone; morphine, codeine, oxycodone, hydrocodone, diamorphine, pethidine, tramadol, buprenorphine, benzocaine, lidocaine, chloroprocaine, tetracaine, procaine, tricyclic antidepressants, amitriptyline, carbamazepine, gabapentin, pregabalin, pantenol, biotin, disodium lauriminodipropionate tocopheryl phosphate, ciclopirox olamine, nordihydroguaiaretic acid and alkylglycerine ethers.

In another aspect, the invention relates to the composition of the invention for use in medicine. Alternatively, the invention relates to the use of the composition of the invention for the manufacture of a medicament.

In a further aspect, the invention relates to the composition of the invention for use in the prevention and/or treatment of skin cancer, actinic keratosis, solar erythema and/or sunburn in a subject. Alternatively, the invention relates to the use of the composition of the invention for the manufacture of a medicament for the treatment and/or prevention of skin cancer, actinic keratosis, solar erythema and/or sunburn in a subject. Furthermore, the invention relates to a method for the treatment of a subject suffering from of skin cancer, actinic keratosis, solar erythema and/or sunburn which comprises administering a therapeutically effective amount of the composition of the invention.

The term "prevention", "preventing" or "prevent", as used herein, relates to the administration of a composition according to the invention or of a medicament comprising said composition to a subject who has not been diagnosed as possibly having a skin cancer, actinic keratosis, erythema solar and/or sunburn at the time of administration, but who would normally be expected to develop said disease or be at increased risk for said disease. The prevention intends to avoid the appearance of said disease. The prevention may be complete (e.g. the total absence of a disease). The prevention may also be partial, such that for example the occurrence of a disease in a subject is less than that which would have occurred without the administration of the composition of the present invention. Prevention also refers to reduced susceptibility to a clinical condition.

The term "treatment", as used herein, relates to the administration of a composition according to the invention or of a medicament comprising said composition to a subject suffering from a skin cancer, actinic keratosis, erythema solar and/or sunburn including the administration in an initial or early stage of a disease, wherein the object is to prevent or slow down (lessen) an undesired physiological change or disorder. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. Treatment also means prolonging survival as compared to expected survival if not receiving the treatment.

The term "skin cancer", as used herein, refers to those cancers that arise from the skin. They are due to the development of abnormal cells that have the ability to invade or spread to other parts of the body. There are three main types: basal cell cancer (BCC), squamous cell cancer (SSC) and melanoma. The first two together along with a number of less common skin cancers are known as non-melanoma skin cancer (NMSC). Basal cell cancer grows slowly and can damage the tissue around it but is unlikely to spread to distant areas or result in death. It often appears as painless raised area of skin, that may be shiny with a small blood vessel running over it or may present as raised area with an ulcer. It usually presents as a hard lump with a scaly top but may also form an ulcer. Melanomas are the most aggressive. Signs include a mole that has change in size, shape, color, has irregular edges, has more than one color, is itchy or bleeds.

The term "actinic keratosis", as used herein, refers to a pre-cancerous patch of thick, scaly or crusty skin. These growths are more common in fair-skinned people and those who are frequently in the sun. They usually form when skin gets damaged by ultraviolet radiation from the sun or indoor tanning beads. Actinic keratosis is considered potentially pre-cancerous; left untreated; it may turn into a squamous cell carcinoma. Untreated lesions have up to 20% risk of progression to squamous cell carcinoma.

The term "solar erythema", as used herein, refers to the inflammation caused by the ultraviolet radiation emitted by the sun (or by a ultraviolet radiation lamp). Ultraviolet radiation kills the cells of the epidermis (keratinocytes) and induces the release of many inflammatory factors which give raise to reddening and itching.

The term "sunburn", as used herein, refers to a form of radiation burn that affects living tissue, such as skin that results from an overexposure to ultraviolet radiation, commonly from the sun. Common symptoms in humans and other animals include red or reddish skin that is hot to the touch, pain, general fatigue and mild dizziness. Typically, there is initial redness (erythema), followed by varying degrees of pain, proportional in severity to both the duration and intensity of exposure. Other symptoms can include edema, itching, peeling skin, rash, nausea, fever, chills and syncope.

The term "therapeutically effective amount" will be defined in the context of the pharmaceutical compositions of the invention.

Pharmaceutical Compositions of the Invention

For their medical uses, the composition of the invention may be found in a pharmaceutical composition. Thus, in another aspect, the invention relates to a pharmaceutical composition comprising a therapeutically effective amount of the composition comprising a DNA repair enzyme and at least one phycobiliprotein and a pharmaceutically acceptable vehicle.

The terms "composition", "DNA repair enzyme" and "phycobiliprotein" as well as the particular embodiments thereof have been defined in the context of the first aspect of the invention and equally applies to the second aspect of the invention.

The term "pharmaceutical composition", as used herein, relates to a composition comprising at least a particle provided by the present invention together with a pharmaceutically acceptable carrier.

The terms "pharmaceutically acceptable vehicle", "pharmaceutically acceptable carrier," "pharmaceutically acceptable diluent" or "pharmaceutically acceptable excipient", used interchangeably herein, refer to a non-toxic solid, semisolid or liquid filler, diluent, encapsulating material or formulation auxiliary of any conventional type. A pharmaceutically acceptable carrier is essentially non-toxic to recipients at the employed dosages and concentrations and is compatible with other ingredients of the formulation. The number and the nature of the pharmaceutically acceptable carriers depend on the desired administration form. The pharmaceutically acceptable carriers are known and may be prepared by methods well known in the art. They are involved in carrying or transporting the subject chemical from one organ, or portion of the body, to another organ, or portion of the body without excessive toxicity, irritation, allergic response, or other problem or complication, commensurate with a reasonable benefit/risk ratio. Each carrier must be "acceptable" in the sense of being compatible with the other ingredients of the formulation and not injurious to the patient. Some examples of materials which can serve as pharmaceutically-acceptable carriers include: (a) sugars (e.g. lactose, glucose and sucrose), (b) starches (e.g. corn starch and potato starch), (c) cellulose and its derivatives (e.g. sodium carboxymethyl cellulose, ethyl cellulose and cellulose acetate), (d) powdered tragacanth, (e) malt, (f) gelatin, (g) talc, (h) excipients (e.g. cocoa butter and suppository waxes), (i) oils (e.g. peanut oil, cottonseed oil, safflower oil, sesame oil, olive oil, corn oil and soybean oil), (j) glycols (e.g. propylene glycol), (k) polyols (e.g. glycerin, sorbitol, mannitol and polyethylene glycol), (l) esters (e.g. ethyl oleate and ethyl laurate), (m) agar, (n) buffering agents (e.g. magnesium hydroxide and aluminum hydroxide), (o) alginic acid, (p) pyrogen-free water, (q) isotonic saline, (r) Ringer's solution, (s) ethyl alcohol, (t) phosphate buffer solutions and (u) other non-toxic compatible substances employed in pharmaceutical formulations. Wetting agents, emulsifiers and lubricants (e.g. sodium lauryl sulfate and magnesium stearate), as well as coloring agents, release agents, coating agents, sweetening, flavoring and perfuming agents, preservatives and antioxidants can also be present in the compositions. Examples of pharmaceutically-acceptable antioxidants include: (a) water soluble antioxidants (e.g. ascorbic acid, cysteine hydrochloride, sodium bisulfate, sodium metabisulfite or sodium sulfite), (b) oil-soluble antioxidants (e.g. ascorbyl palmitate, butylated hydroxyanisole (BHA), butylated hydroxytoluene (BHT), lecithin, propyl gallate or α-tocopherol), and (c) metal chelating agents (e.g. citric acid, ethylenediamine tetraacetic acid (EDTA), sorbitol, tartaric acid or phosphoric acid).

The term "therapeutically effective amount", as used herein, relates to the sufficient amount of a compound (i.e of the composition of the invention) to provide the desired effect and it will generally be determined, by among other causes, the characteristics of the compound itself and the therapeutic effect to be achieved. It will also depend on the subject to be treated, the severity of the disease suffered by said subject, the chosen dosage form, administration route, etc. For this reason, the person skilled in the art must adjust the doses depending on the aforementioned variables.

The pharmaceutical composition of the invention can be administered by topical, transdermal orsubcutaneous route. Illustrative examples of topical or transdermal administration include but are not limited to iontophoresis, sonophoresis, electroporation, mechanical pressure, osmotic pressure gradient, occlusive dressing, microinjections, needleless injections by means of pressure, microelectric patches and any combination thereof. In any case, the excipients will be chosen depending on the pharmaceutical dosage form selected.

In a particular and preferred embodiment of the invention, the pharmaceutical composition of the invention is administered by topical route. For topical administration, the pharmaceutical compositions of the invention can be formulated as creams, gels, lotions, liquids, pomades, spray solutions, dispersions, solid bars, emulsions, microemulsions and similars which may be formulated according to conventional methods that use suitable excipients, such as, for example, emulsifiers, surfactants, thickening agents, coloring agents and combinations of two or more thereof.

Additionally, pharmaceutical compositions of the invention may be administered in the form of transdermal patches or iontophoresis devices. Suitable transdermal patches are well known by the person skilled in the art.

Several drug delivery systems are known and can be used to administer the compounds or compositions of the invention, including, for example, encapsulation in liposomes, microbubbles, emulsions, microparticles, microcapsules, nanoparticles, nanocapsules and similars. The required dosage can be administered as a single unit or in a sustained release form. In a particular and preferred embodiment of the invention, the pharmaceutical composition is encapsulated in liposomes.

Sustainable-release forms and appropriate materials and methods for their preparation are well known in the state of the art.

In a particular embodiment, the pharmaceutical composition provided by the present invention comprises between 0.001% and 99.998% by weight of the active product of the invention (i.e the composition comprising a DNA repair enzyme and at least one phycobiliprotein).

Cosmetic Compositions of the Invention

In another aspect, the invention relates to a cosmetic composition comprising a cosmetic effective amount of the composition comprising a DNA repair enzyme and at least one phycobiliprotein and a cosmetically acceptable vehicle.

The terms "composition", "DNA repair enzyme" and "phycobiliprotein" as well as the particular embodiments thereof have been defined in the context of the composition of the invention and equally applies to the cosmetic compositions of the invention.

The term "cosmetic composition" or "personal care composition", as used herein, refers to a composition suitable for use in personal hygiene of human beings or animals, or in order to enhance the natural beauty or change the body appearance without affecting the structure or functions of the human or animal body, comprising one or more products providing such effects. If desired, the cosmetic composition provided by the invention can contain, in addition to the active product of the invention, one or more cosmetics or cosmetic products, i.e., substances or mixtures intended to be placed in contact with the external parts of the human or animal body (e.g., epidermis, hair system, nails, lips, etc.) or with the teeth and the buccal mucosa, for the exclusive or main purpose of cleaning them, perfuming them, changing their appearance, protecting them, keeping them in good condition or correcting body odors. Illustrative examples of cosmetically acceptable vehicles include the products contained in the INCI (International Nomenclature of Cosmetic Ingredients) list. Cosmetic or personal care compositions include products such as balms, pads, pomades, creams, etc. oils, surfactants, humectants, botanical extracts, vitamins, antioxidants, sunscreen agents, perfumes, preservatives, and the like. Illustrative examples of humectants, botanical extracts, vitamins, antioxidants and sunscreen agents have been detailed in the context of the composition of the invention.

The ingredients as described hereinabove are preferably provided in a cosmetic composition that may be formulated into a cream, gel, lotion, oil, ointment, powder, stick, cake, or other forms that can be topically applied. The resulting cosmetic composition may be in the form of a liquid, solid, semi-solid, dispersion, suspension, solution or emulsion, and it can be either aqueous-based or anhydrous. The cosmetic compositions of the invention may also be in the form of color cosmetic compositions, such as foundation makeup, mascara, lip color, blush, eye shadow, and the like. Certain other derivatives are lipophilic in nature and will more likely be found in the oil phase of the emulsion. The DNA repair enzyme is preferably found in the water phase of the emulsion or encapsulated in an aqueous phase within liposomes.

The cosmetic compositions of the invention in the form of skin creams or lotions typically comprise from about 5-98% water, 1-85% oil, and from about 0.1 to 20% of one or more surfactants.

The cosmetic compositions of the invention in the form of color cosmetic compositions such as foundations, blush, eye shadow and the like may be in the anhydrous or aqueous form. If aqueous based, such compositions will preferably contain from about 5-98% water, 1-85% oil, and optionally from about 0.1 to 20% of one or more surfactants in addition to from about 0.1% to 65% of particulates that are pigments or a combination of pigments and powders. If anhydrous, the cosmetic compositions may contain from about 0.1% to 95% oil, from about 0.1% to 99% particulates, and optionally from about 0.1% to 50% of one or more structuring agents.

The cosmetic compositions of the invention in the form of mascara compositions generally contain from about 5-98% water, 1-85% oil, and from about 0.1% to 20% surfactant in addition to natural or synthetic polymers that are film forming, such as aqueous dispersions of acrylic copolymers, aqueous dispersions of polyurethane, or silicone resins.

The cosmetic compositions of the invention in the form of lip color compositions are generally in the form of sticks or glosses, and may comprise from about 0.1% to 95% oil, from about 0.1% to 60% structuring agent, and from about 0.1% to 50% particulates.

The cosmetic compositions of the invention in the form toner compositions typically comprise from about 0.1% to 99% of water or other polar nonaqueous solvent such as ethanol, propylene glycol, butylene glycol. Toners are typically applied for cleansing purposes using a cotton pad or other applicator to swipe across the skin to remove debris or dirt.

The cosmetic compositions of the invention in the form of spritzer compositions typically include those that may be sprayed on the skin. Preferably such compositions will contain from about 0.1% to 99% of water or other polar nonaqueous solvent. Such compositions are generally applied as leave on compositions.

The cosmetic compositions of the invention in the form of gels may be aqueous based and may contain from about 0.1% to 95% water, from about 0.1% to 50% structuring agents.

The term "cosmetic effective amount", as used herein, relates to the sufficient amount of a compound (i.e of the composition of the invention) to provide the desired effect and it will generally be determined, by among other causes, the characteristics of the compound itself and the cosmetic effect to be achieved. The dosage for obtaining a cosmetic effective amount it will also depend on a range of factors, such as, for example, age, weight, sex or tolerance of the animal, preferably a mammal and more preferably human.

In a particular and preferred embodiment of the invention, the cosmetic composition of the invention is administered by topical route. Adequate formulations for topical administration of the composition of the invention have been detailed in the context of the pharmaceutical compositions of the invention and equally apply to the cosmetic composition of the invention.

If desired, the pharmaceutical or cosmetic composition of the invention is incorporated in a fabric, a non-woven fabric or a medical device. Illustrative examples of said fabric, non-woven fabric or medical device include but are not limited to bandages, gauzes, t-shirts, panty hose, socks, underwear, girdles, gloves, diapers, sanitary napkins, dressings, bedspreads, towelettes, adhesive patches, non-adhesive patches, occlusive patches, microelectric patches and face masks.

In a particular embodiment, the cosmetic composition provided by the present invention comprises between 0.001% and 99.998% by weight of the active product of the invention (i.e the composition comprising a DNA repair enzyme and at least one phycobiliprotein).

Cosmetics Methods of the Invention

In another aspect, the invention relates to a cosmetic method for preventing premature-aging on skin which comprises administering a cosmetic composition comprising a cosmetic effective amount of the composition of the invention and a cosmetically acceptable vehicle.

The terms "composition", "DNA repair enzyme, "phycobiliprotein" and "prevention" as well as the particular embodiments thereof have been defined in the context of the composition of the invention and equally applies to the cosmetic methods of the invention. The terms "cosmetic composition", "cosmetic effective amount" and "cosmetically acceptable vehicle" have been explained in the context of the cosmetic compositions of the invention and are equally used in the cosmetic methods of the invention.

The term "premature-aging on skin" as used herein refers to the signs related to an aged skin which appears in a young skin. The main esthetical sings of skin aging are wrinkling, sagging, apparent thinning, appearing of age spots and decrease of elasticity. Cutaneous aging occurs through two biologically distinct processes: intrinsic and extrinsic aging. The first is a naturally occurring process that results from slow tissue degeneration. In human dermis, intrinsic aging is characterized by three features: atrophy of the dermis due to loss of collagen, degeneration in the elastic fiber network, and loss of hydration. These three features often manifest themselves by a number of symptoms comprising, among others, decline of skin elasticity, rough skin, skin wrinkling, sagging, apparent skin thinning, and pigmentation. In contrast to intrinsic aging, extrinsic aging or premature aging on skin is due to environmental factors such as, ultraviolet radiation, reactive oxygen species (ROS) and stress, which generates rough wrinkles in the skin surface and significantly decreases skin elasticity. The cosmetic method of the invention helps to prevent the premature aging process on skin.

In a particular and preferred embodiment of the cosmetic method of the invention, the cosmetic composition is topically administered. Adequate formulations for topical administration of the composition of the invention have been detailed in the context of the pharmaceutical compositions of the invention and equally apply to the cosmetic method of the invention.

The following example is provided as merely illustrative and is not to be construed as limiting the scope of the invention.

EXAMPLE 1

Synergistic Effects of Photolyase and Phycocianin-C in the Protection of Cells from UV Damage Cell Culture Conditions Human skin fibroblasts (BJ, ATCC-CRL-2522) were cultured in MEM (PAA) supplemented with 10% FCS (Invitrogen) plus 2 mM L-glutamine. Cells were cultured at 37° C. in a humidified 5% $CO_2$-atmosphere, and were consistently free of mycoplasma as evaluated by EZ-PCR mycoplasma test kit (Biological Industries).

All experiments were carried out at 80-85% of confluence, with the same batch of cells.

UV Damage and MTT Analysis

BJ cells were plated onto 24-well cell culture dishes ($7\times10^4$ cells/well) in 1 ml of culture medium. Twenty-four hours later, cells were washed twice with PBS and were irradiated with 500 J/m2 of UVB in ml of PBS. Then cells were treated with products (Photolyase encapsulated in liposomes, phycocyanin encapsulated in liposomes, and GenoFix® CPD, which is Anacystis nidulans extract containing photolyase and phycocyanin encapsulated in liposomes) at 1-2-3% in 2 ml of PBS. Photolyase and phycocyanin were at equimolar concentration in all the tested conditions in a 1:6 ratio. After one hour cells were treated under white light for 1 hour to allow photorepair by photolyase and then cells were incubated in serum-free medium for additional 48 hours. Cell viability was subsequently assessed using the MTT assay. In brief, after removing the culture medium cells were incubated with a 5 mg/mL solution of methylthiazolyldiphenyl-tetrazolium bromide (MTT). After two hours, the MTT solution was removed and substituted by DMSO. Finally, absorbance was measured at 550 nm using a spectrophotometer.

Results

|  | 1% | 2% | 3% |
| --- | --- | --- | --- |
| Encapsulated photolyase | 4,786471768 | 11,69074233 | 12,26712525 |
| Encapsulated phycocyanin | 9,977070794 | 13,94468329 | 13,15849814 |
| GenoFix ® CPD | 19,57580969 | 30,49584408 | 32,07623961 |

Results have been expressed in percentage of survival compared to Control (treated with UVB and UVA).

Example 2: Immunosuppressive Effect of Photolyase and Phycocianin-C

The combination of DNA repair enzymes with phycobiliproteins shows enhanced protective and restorative activity regarding, at least, the immunosuppressive effect of UV radiation through reducing the secretion of IL-6 (which is a TNF-alpha secretion inducer) by fibroblasts and the reduction of matrix-degrading enzymes such as MMP-1.

Following experimental procedures described above, cells treated with equimolar concentrations of either encapsulated photolyase, encapsulated phycocyanin or GenoFix-CPD™, were analyzed for the release of IL-6 and of MMP-1. IL-6 release was measured in culture supernatants after 24 h of photorepair by means of a commercial ELISA kit following instructions of the manufacturer (Life technologies, Ref. KMC0061). MMP-1 presence and activity was analyzed after 72 h of photorepair by gelatin zymography analysis performed as described previously (Pazzaglia et al., 2004) with the following modifications: Treated cells were maintained 24 h or 48 h at 37° C. in serum free medium to analyze their capacity to increase the secretion of active forms of matrix metalloproteinases (MMPs). After this, supernatants were centrifuged to remove the debris. Then, 10 µL of Laemmli sample buffer without reducing agent (80 mM Tris-HCl, pH 6.8, 4% SDS, 10% glycerol, 0.01% bromophenol blue) was added to 10 µl of each clear supernatants that were loaded without boiling in a 8% SDS-polyacrylamide gel copolymerized casein from bovine milk, at a final concentration of 1 mg/mL. After electrophoresis, SDS was removed by washing the gel three times for 15 minutes with 2.5% Triton X-100 in $H_2O$. Activation was developed by incubation for 48 h of the gel at 37° C. in the presence of 50 mM Tris-HCl, pH 7.5, 10 mM $CaCl_2$) and 0.02% $NaN_3$. Staining was performed for 1 hour at RT with 0.1% naphthol amido black (Sigma) in acetic acid, methanol and water at a proportion of 1:3:6 in volume. Then, gels were washed with destaining solution (acetic acid, methanol and water at a proportion of 1:3:6 in volume) until clear bands were observed over a dark background. Bands were quantified using the NIH ImageJ imaging software.

Results:

|  | MMP-1 | | IL-6 | |
| --- | --- | --- | --- | --- |
|  | 1% | 3% | 1% | 3% |
| Encapsulated photolyase | 39,88100585 | 19,0424964 | 55,71705426 | 28,10077519 |
| Encapsulated phycocyanin | 4,242109351 | 22,72282657 | 7,59392486 | 44,56434852 |
| GenoFix ® CPD | 54,8211756 | 37,69778186 | 57,35411671 | 80,53557154 |

The invention claimed is:

1. A composition comprising a DNA repair enzyme and at least one phycobiliprotein, wherein said DNA repair enzyme is a photolyase, wherein said photolyase and said phycobiliprotein is encapsulated by liposomes, and wherein the percentage by volume of the DNA repair enzyme in the composition is from 1% to 3% and wherein the percentage by volume of the phycobiliprotein in the composition is from 1% to 3%.

2. The composition according to claim 1, wherein said photolyase is selected from the group consisting of: *Anacystis nidulans* photolyase, *Dunaliella salina* photolyase, *Haematococcus pluvialis* photolyase, *Botryococcus* sp. photolyase, *Chlorella* sp. photolyase, *Porphydium* sp. photolyase, *Spirulina* sp. photolyase, *Hordeum* sp. photolyase, *Zea mays* photolyase, *Triticum* sp. photolyase, *Nicotiana* sp. photolyase and *Arabidopsis thaliana* photolyase.

3. The composition according to claim 1, wherein said photolyase is an *Anacystis nidulans* photolyase.

4. The composition of claim 1, wherein said phycobiliprotein is selected from the group consisting of C-phycocianin, allophycocianin, B-phycoerithrin and mixtures thereof.

5. The composition of claim 1, wherein said phycobiliprotein is an *Anacystis nidulans* phycobiliprotein.

6. A cosmetic composition comprising a cosmetic effective amount of the composition of claim 1 and a cosmetically acceptable vehicle.

7. A pharmaceutical composition comprising a therapeutically effective amount of the composition of claim 1 and a pharmaceutically acceptable vehicle.

8. A cosmetic method for preventing premature-aging on skin which comprises administering to a subject the cosmetic composition according to claim 6.

9. The cosmetic method according to claim 8, wherein said cosmetic composition is topically administered.

10. A method for the prevention and/or treatment of skin cancer, actinic keratosis, solar erythema and/or sunburn in a subject in need thereof comprising the administration to said subject a composition of claim 1.

* * * * *